US00PP20913P3

(12) United States Plant Patent
Dressel

(10) Patent No.: US PP20,913 P3
(45) Date of Patent: Apr. 6, 2010

(54) GRAPEVINE PLANT NAMED 'CRIMSON CABERNET'

(50) Latin Name: *Vitis vinifera*
Varietal Denomination: Crimson Cabernet

(76) Inventor: Lucian W. Dressel, R.R. 2, Suite 207, Carrollton, IL (US) 62016

( * ) Notice: Subject to any disclaimer, the term of this patent is extended or adjusted under 35 U.S.C. 154(b) by 0 days.

(21) Appl. No.: 11/978,501

(22) Filed: Oct. 30, 2007

(65) Prior Publication Data

US 2009/0113577 P1 Apr. 30, 2009

(51) Int. Cl.
*A01H 5/00* (2006.01)

(52) U.S. Cl. ..... Plt./205

(58) Field of Classification Search ..... Plt./205
See application file for complete search history.

*Primary Examiner*—Kent L Bell

(57) ABSTRACT

A new and distinct, self rooted, variety of grapevine plant, 'Crimson Cabernet', from a cross of 'Cabernet Sauvignon' and 'Norton', which can be distinguished by its outstanding wine combined with high productivity, disease resistance, and cold hardiness superior to one of its two acclaimed parents 'Cabernet Sauvignon'.

6 Drawing Sheets

Botanical classification: *Vitis vinifera* ('Cabernet Sauvignon' crossed with 'Norton').

Varietal denomination: 'Crimson Cabernet'.

BACKGROUND OF THE INVENTION

Most grape varieties used for production of high quality wines around the world are of the species *Vitis vinifera*. These *V. vinifera* varieties, when cultivated in northern regions of the United States with a continental climate are often subject to serious injury or death from low temperatures during winter. *V. vinifera* must also be grafted onto an American rootstock in order to be grown successfully. Although several wild *Vitis* species occur in colder regions of North America and eastern Asia, the wine made from these species generally has serious defects. Thus, a great need existed for grape plants that would combine the superior wine quality of *V. vinifera* with the cold weather resistance and disease resistance of wild species yet be free of their unpleasant wild flavors. A grape breeding program conducted by Lucian W. Dressel at Davis, Calif. and at Winters, Calif. from 2000 to 2002 developed such varieties by combining various *V. vinifera* with the native grape plant known as 'Norton' (aka 'Cynthiana').

BRIEF SUMMARY OF THE INVENTION

The invention is a new and distinct variety of grape plant designated 'Crimson Cabernet' which produces dark black fruit highly suitable for red wine production, and has a combination of high wine quality, excellent cold hardiness, disease resistance, good productivity, and does not need to be grafted. It has proven to be well adapted to various states including California, Missouri, Illinois, Kentucky and Iowa. 'Crimson Cabernet' resulted from a cross of 'Cabernet Sauvignon' and 'Norton' made in 2001 in Winters, Calif.

'Crimson Cabernet' propagates moderately well from hardwood cuttings. Once rooted however the young plants quickly become established and all 'Crimson Cabernet' plants propagated in this manner have been genetically stable, producing only dark black fruit with dark reddish bluish juice. The vines of 'Crimson Cabernet' have an abundance of tendrils and easily adapt themselves to a high wire cordon trellis system. Canes have a drooping growth attitude and are easily combed and trained. The bud break and bloom of 'Crimson Cabernet' are very late, typically after that of both 'Cabernet Sauvignon' and 'Norton'. Its flowers are perfect and self fertile. 'Crimson Cabernet' vines typically set a moderate to heavy crop. The fruit of 'Crimson Cabernet' is borne on medium sized clusters that are tight, compact and have a small very detached wing when mature. The peduncles are 'Norton'-like being very long. Where the five main veins join the petiole, the base of the veins (on the back side of the leaves) has a distinctive red color that forms a five pointed red "star". The berries are small to medium in size with a waxy bloom at maturity. Berry splitting and bunch rot have not been observed to date, nor has crown gall. In commercial vineyards on a normal spray schedule no disease problems have been noted from Black Rot, Downey Mildew, Powdery Mildew, or any other fungus disease or insects. Resistance to Pierce's Disease is unknown, but is being tested in Louisiana.

The fruit of 'Crimson Cabernet' can be fermented to produce a dry red wine that can be barrel aged to produce a wine in the classic style of a red Bordeaux or California 'Cabernet Sauvignon'. The wine has none of the flavors associated with wines made from either French hybrid grapes or *V. labrusca* varieties. 'Crimson Cabernet''s wine is deep crimson red and bright. The nose is reminiscent of cassis, dried cherries, and cedar, with some hints of evergreen. The taste is full bodied, clean, spicy with hints of rosemary, blackberries and currents.

'Crimson Cabernet' is much more cold hardy than its parent 'Cabernet Sauvignon' and has the advantage of being self rooted so that even if the plant is killed to the ground it can be renewed from an underground sucker, unlike 'Cabernet Sauvignon'. Unlike its other parent, 'Norton', its growth habits are quite orderly and manageable and 'Crimson Cabernet' does not have to be grown on a double curtain system to be profitable.

BRIEF DESCRIPTION OF THE FIGURES

FIG. 1—'Crimson Cabernet' Leaf Front—A photograph showing the front view of a 'Crimson Cabernet' leaf.

FIG. 2—'Crimson Cabernet' Leaf Rear—A photograph showing the rear view of a 'Crimson Cabernet' leaf.

FIG. 3—'Crimson Cabernet' Vine—A photograph showing trunk, canes, leaves and fruit after verasion in 2006.

FIG. 4—'Crimson Cabernet' Bunches—A photograph of 'Crimson Cabernet' showing a close up of three typical fruit cluster after verasion, Aug. 31, 2006.

FIG. 5. 'Crimson Cabernet' Grow Tip—A photograph from Jul. 27, 2007 showing the growing tip, tendrils and shoot from 'Crimson Cabernet'.

FIG. 6. 'Crimson Cabernet' Wing—A photograph showing a typical bunch from 'Crimson Cabernet' with a satellite wing.

The colors in the photographs are as close as possible with the photographic and printing technology utilized. The color values cited in the detailed botanical description accurately describe the colors of the new grape.

DETAILED BOTANICAL DESCRIPTION OF THE INVENTION

The following descriptions of 'Crimson Cabernet' apply to vines planted in Carrollton, Ill. in 2004. When dimensions, sizes, colors and other characteristics are given, it is to be understood that such characteristics and approximations set forth as accurately as possible. Variations of the usual magnitude incident to climatic factors, fertilization, pruning, pest control and other cultural practices are to be expected.

The colors referred to in this abstract are those of The Royal Horticultural Society Colour Chart, copyrighted 2005.

VINE

General:

*Size.*—The test grapevines of 'Crimson Cabernet' are planted approximately 8 feet apart down the row and 10 feet apart between the rows. The vine canopy extends from 0.75 meters to 1.0 meters out into the row. The vines are in their fourth leaf.

*Vigor.*—When first planted, much more vigorous than 'Norton'. When mature equally vigorous as 'Cabernet Sauvignon' but without the rampant and unruly growth habits of 'Norton'.

*Productivity.*—Productive, bearing 4 tons to 6 tons per acre depending on pruning and growing conditions.

Trunk:

*Surface texture.*—Rough textured and furrowed and only slightly shaggy.

*Bark color.*—Brownish. Varies from (200A) to (202A).

*Trunk circumference.*—Very straight, round, and uniform in diameter ranging from 2.4 cm to 2.7 cm at 40 cm height from ground to 2.2 cm to 2.5 cm at 600 cm from the ground.

MATURE CANES

Size:

*Thickness.*—Canes that arise from dormant spurs vary from 6 mm to 14 mm at 5 cm to 40 cm from bud. Canes are relatively uniform in width, like 'Norton' and do not taper like Vidal.

Surface: Smooth often finely striated.

Color: Canes are reddish brown on top (45A) and light green underneath (145A).

Internode length: Varies widely depending on type of arm, position on vine and the nature of the bud from which each cane arose. From 3 cm to 4 cm on smaller shorter arms and laterals and from 10 cm to 15 cm on larger canes.

Varies from 9 cm to 14 cm on the stronger upper suncanes and from 3 cm to 5 cm on lateral canes.

TENDRILS

Relatively long ranging from 14 cm to 30 cm.

*Diameter.*—Varies from 1.0 mm to 2.0 mm in thickness measured at the base of the tendril.

*Distribution.*—Discontinuous.

*Form.*—Predominately bifid, although trifid tendrils may be present.

*Color.*—Reddish brown (45A).

GROWING TIPS

Straight, and uniformly green (137C).

LEAVES

Mature leaves:

*General.*—Like its parent 'Norton', the leaves of 'Crimson Cabernet' can have a wide variety of shapes and sizes on the same plant. Variations can be caused by the age of the vine, the location where grown, the weather and any number of other factors.

*Average leaf length.*—11 cm measured from the apex of the central lobe to the bottom of the petiole junction.

*Average leaf width.*—14 cm measured at center of leaf, 6 cm from apex and at a 45 degree angle to central vein:

*Apex of leaf.*—Length of apex 7 cm; width of apex 7 cm. Pointed tooth on top of apex averaging 1.5 cm in length. Remaining teeth on apex are medium 1.5 cm in length and 1.5 cm in width and pointed.

*Base of Leaf.*—Rounded, gradually sloping upwards, approximately 9 cm wide. General shape of petiole sinus V shaped: 3.5 cm long on average mature leaf, 2.0 cm wide at base.

*Shape of upper leaf sinus.*—Large 5 cm in length, 7 mm in width at base.

*Leaf margins.*—Serrate with regular teeth, commonly approximately 18 teeth to 20 teeth per lobe, and approximately 90 teeth to 100 teeth on entire leaf.

*Average blade length.*—11 cm as measured from the apex of the center leaf lobe to the petiole junction.

*Average blade width.*—Typically 14 cm at widest point.

*Blade lobes.*—Almost always having 5 well defined lobes.

*Shape.*—Orbicular. Galet coordinates: 035-2-48 Shape of teeth along leaf margins: Convex.

*Length of teeth along leaf margins.*—Medium to large and variable, 6 mm to 14 mm in length.

*General shape of petiole sinus.*—V shaped on young leaves. Mature leaves' petiolar sinuses show a tennis racket shape.

*Shape of upper leaf sinus.*—Varies from open V shaped to closed overlapping pattern typical of 'Cabernet Sauvignon' where sinuses appear like holes in the leaf.

Leaf color:

*Upper leaf surface.*—Glabrous, rough (137C).

*Lower leaf surface.*—Rather dull and lighter in intensity of color (137C).

*Upper leaf veins.*—Yellowish-green (2C) with a blush of red color (44A) on the five main veins from the petiole junction to the first main vein.

*Lower leaf veins.*—The color of the five main veins from the petiole sinus to the first branching vein is distinctly red (44A), beyond which they are yellow-green (2C).

*Surface texture.*—Rough, glabrous.

*Surface appearance.*—Dull.

*Lower surface texture.*—Rough, dull.

*Length of leaf petiole.*—12 cm.

*Leaf petiole thickness.*—3.0 mm to 4.0 mm measured at mid petiole.

*Leaf petiole shape.*—Glabrous, smooth.

*Leaf petiole color.*—Reddish-brown (172A).

*Length of leaf petiole compared to mid vein.*—On average about the same length.

FLORAL CLUSTER DESCRIPTION

*Bloom timing.*—Varies widely from year to year. Generally late, slightly after 'Norton'. May 10$^{th}$ in 2006.

*Cluster form.*—Conical usually with wings.

*Clusters per shoot.*—Usually three.

*Floral cluster length.*—Average 80 cm.

*Floral cluster width.*—Average 30 cm.

*Cluster peduncles.*—Length 10 cm to 12 cm, thickness 3.0 cm to 4.0 cm

*Peduncle color.*—Green when growing (152D), brown (22C) when mature.

*Inflorescence.*—Hermaphroditic.

*Floral stamens.*—Upright with typically observed anthers 2 mm in length and 0.5 mm in width.

*Flower length.*—2 mm in average flower.

*Flower diameter.*—1 mm in average flower.

*Flower petals.*—Five in number, and open from the bottom to the top. Remaining entire after separation. Petals ovoid in shape with 5 sections remaining attached to one another after falling to ground, 3 mm in diameter. Apex of petals is concave with reddish dot (41A). in center of petal clusters. Base is smooth and 2.5 mm in circumference. Margins are smooth and convexly curved. Color on top surface of petals is grass green (145C). Color on underside of petals is light green (149D).

*Sepals.*—Five in number, and commonly very poorly developed or nonexistent. If present, appearing as little more than a dusty residue with a light green color (149D).

*Pollen amount.*—Abundant.

*Pollen color.*—Pale yellow (8C).

*Calyptras separation from the flower base.*—Complete.

*Duration of bloom.*—Average 10 days to 12 days depending on ambient temperatures during the bloom period.

FRUIT DESCRIPTION — PRIMARY CLUSTERS

*Date of maturity.*—September 9, 2006 in west central Illinois.

*Bunch length.*—12 cm to 25 cm, not including the peduncle.

*Bunch width.*—10 cm to 15 cm.

*Bunch form.*—Conical with a noticeable satellite wing. Whereas 'Norton' will abandon 90% of its wings leaving a scar in its very long peduncle, 'Crimson Cabernet' will usually bear a small round cluster of grapes.

*Bunch weight.*—Average from 90 gm to 150 gm.

*Bunch density.*—Tight like 'Norton'.

*Peduncle length.*—Long like 'Norton' from 5 cm to 8 cm.

*Peduncle thickness.*—Ranges from 3.0 cm to 5.0 cm at the peduncle base.

*Berry form.*—Round.

*Cross sectional view berry form.*—Globose.

*Berry size.*—Small to medium 10 mm to 12 mm in diameter.

*Berry weight.*—2 gm to 5 gm.

*Berry uniformity.*—Excellent.

*Berry pedicel color.*—Very light yellow (158D).

*Berry pedicel length.*—5 mm to 6 mm.

*Berry pedicel thickness.*—1 mm to 2 mm.

*Berry pedicel length.*—5 mm to 6 mm.

*Berry pedicel thickness.*—1 mm to 2 mm.

*Attachment.*—Very strong with no shatter at commercial maturity.

*Berry skin color.*—Black (202A) with waxy bloom (192B). 100% colored.

*Berry skin thickness.*—Medium 0.75 mm.

*Berry skin surface texture.*—Smooth and glabrous.

*Berry skin, tenacity to flesh.*—Skin is tenacious to the flesh.

*Berry skin, tendency to crack.*—Has never shown any cracking.

*Berry skin, reticulation.*—Surface is smooth with no reticulations present.

*Berry color.*—Black (202A).

*Berry surfaces.*—Uniformly covered with a waxy, grayish bloom (192B).

*Berry flesh color.*—Light translucent green (145C).

*Juiciness of flesh.*—Similar to standard commercial wine varieties. Much juicier than 'Norton', not as juicy as 'Cabernet Sauvignon'.

*Berry firmness.*—Very firm.

*Berry juice.*—Clear, tart, and slightly pinkish at crushing (27D).

*Solids-sugar percentage* (*at maturity*).—22.0 on Sep. 12, 2006.

*pH of berry juice.*—3.18 on Sep. 12, 2006.

*Titratable acidity.*—7.75 gm/liter.

*Seed.*—Viable, 3 seeds per berry to 4 seeds per berry, average size and shape for *V. vinifera,* 6.5 mm in length and 3.5 mm in width.

*Flavor.*—Good, tart, sweet, typical *V. vinifera* red wine grape flavor.

*Aroma.*—Typical crushed red wine grape aroma. No wild aromas.

SECONDARY BUNCHES

Almost no secondary bunches have been observed in normal years with no spring frost.

COMPARISON BETWEEN PARENTAL AND COMMERCIAL CULTIVARS

The physical appearance of the vine of 'Crimson Cabernet' more closely resembles that of its parent 'Cabernet Sauvignon'. Like 'Cabernet Sauvignon' the leaves of 'Crimson Cabernet' are more modest in size and show fewer variations than do the leaves of its parent 'Norton'. The growth habits are more orderly than 'Norton' and it can produce normal crops of between 4 tons to 6 tons per acre without having to be grown on a double curtain trellis system. 'Crimson Cabernet' is far more resistant to the endemic vine diseases of the eastern U.S. than 'Cabernet Sauvignon' and it can be grown on its own roots.

The berries and bunches are much larger than 'Norton' and the berries have fewer seeds making wine making easier.

COMPARISON BETWEEN CABERNET DIANE AND 'CRIMSON CABERNET'

The Vines:

'Cabernet Diane' and 'Crimson Cabernet' are sister vines from the same cross of 'Norton'×'Cabernet Sauvignon' and as expected would have many features in common. Each is a distinctly different vine, however, both in the vineyard and in wine character. Grown side by side the most noticeable difference is in the leaves. Most of the leaves of 'Crimson Cabernet' are lobed, somewhat like its parent 'Cabernet Sauvignon', although some non lobed leaves are always present. 'Cabernet Diane' is the exact opposite with most of its leaves being non lobed although it has the occasional lobed leaf. The petioles of 'Cabernet Diane' also tend to be much redder in color than those of 'Crimson Cabernet'.

The Fruit:

The bunches of 'Crimson Cabernet' tend to be conical and usually have a small satellite wing. The bunches of 'Cabernet Diane' are more triangular in shape.

The Wine:

'Crimson Cabernet''s wine is soft and smooth, early maturing and resembles that of 'Merlot'. 'Cabernet Diane''s wine is spicier and often has a bouquet not unlike that of 'Cabernet Franc' with a slight pleasant aroma of the wood from pencil shavings.

The invention claimed is:

1. A new and distinct variety of grapevine plant as illustrated and described.

* * * * *

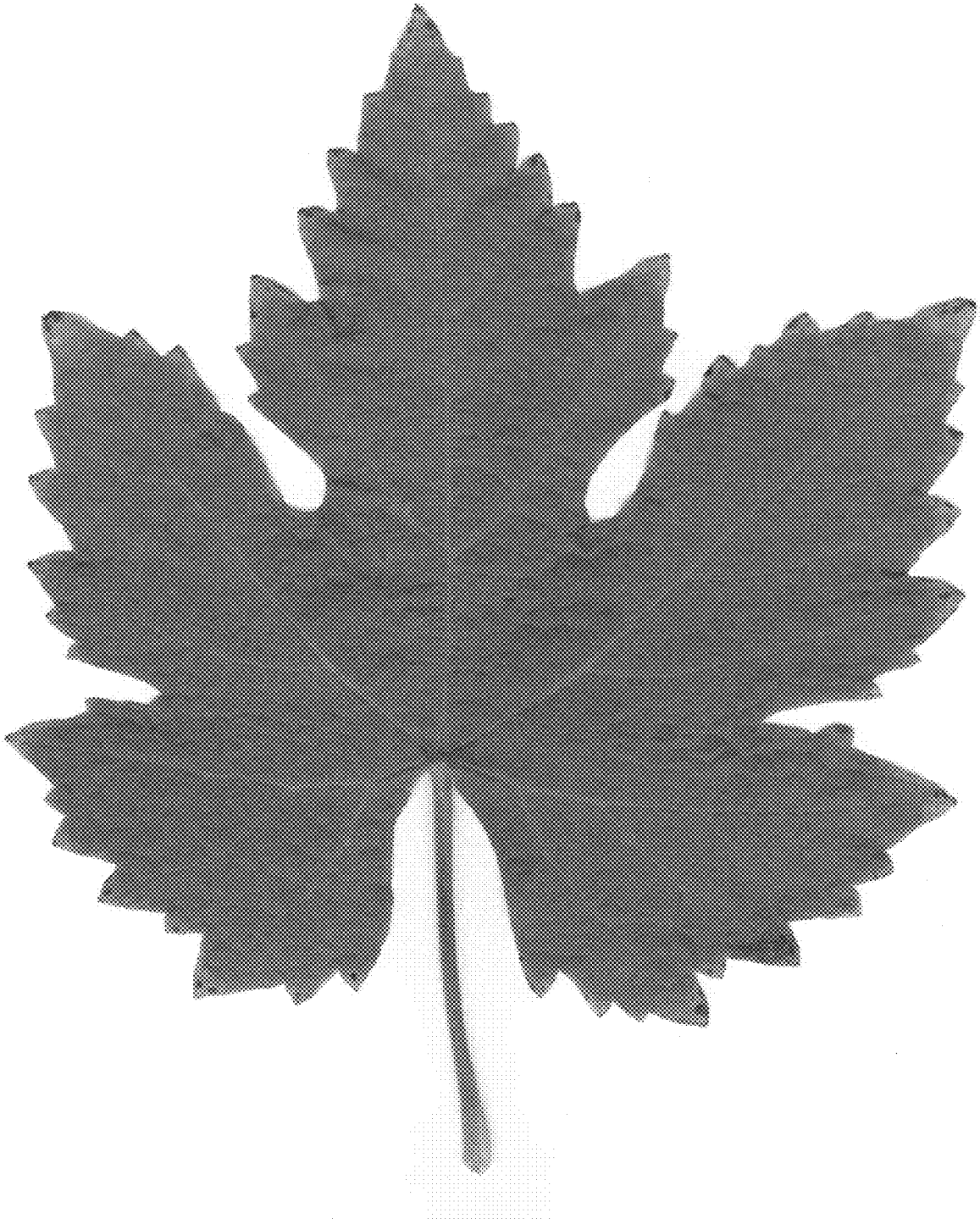

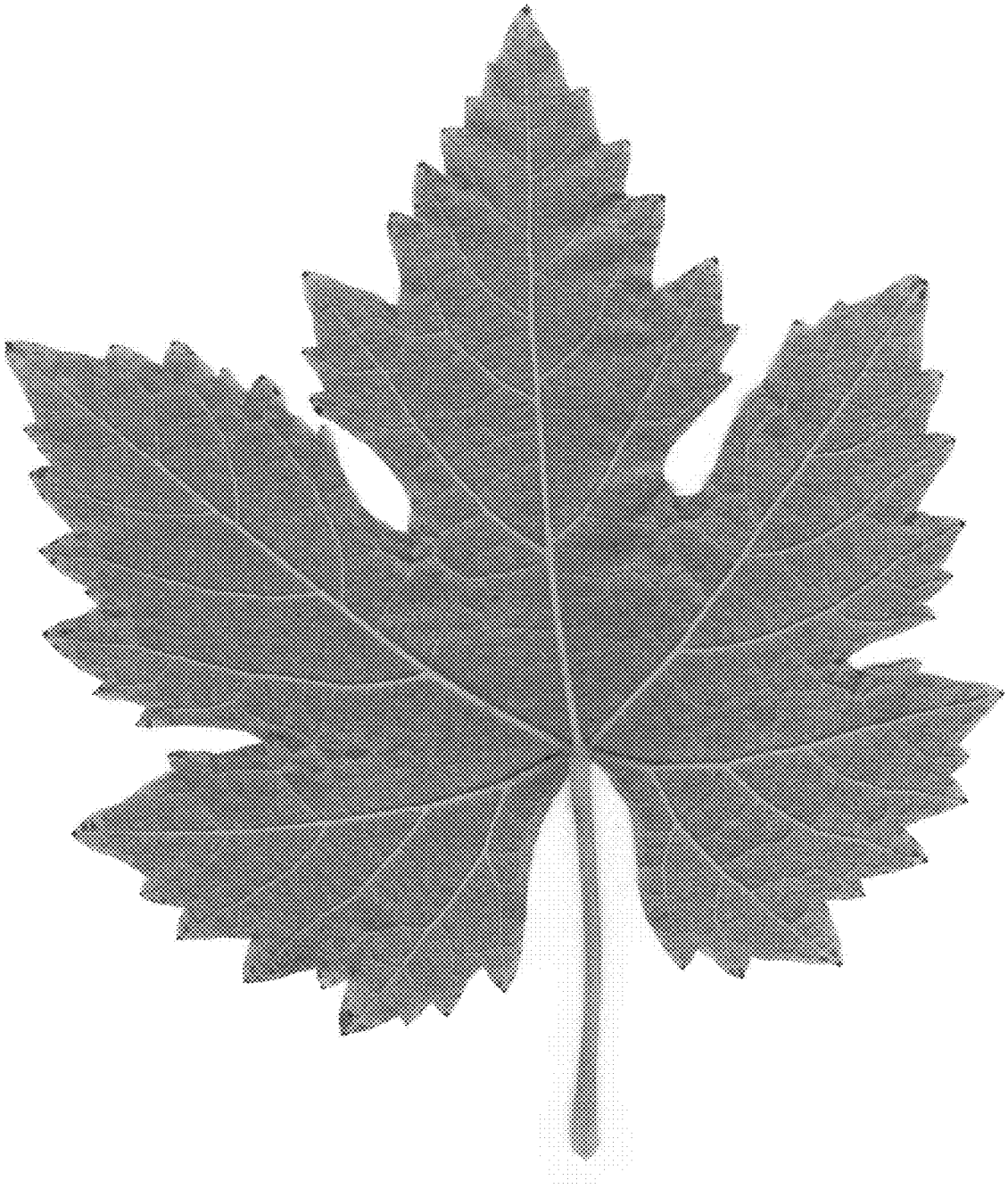

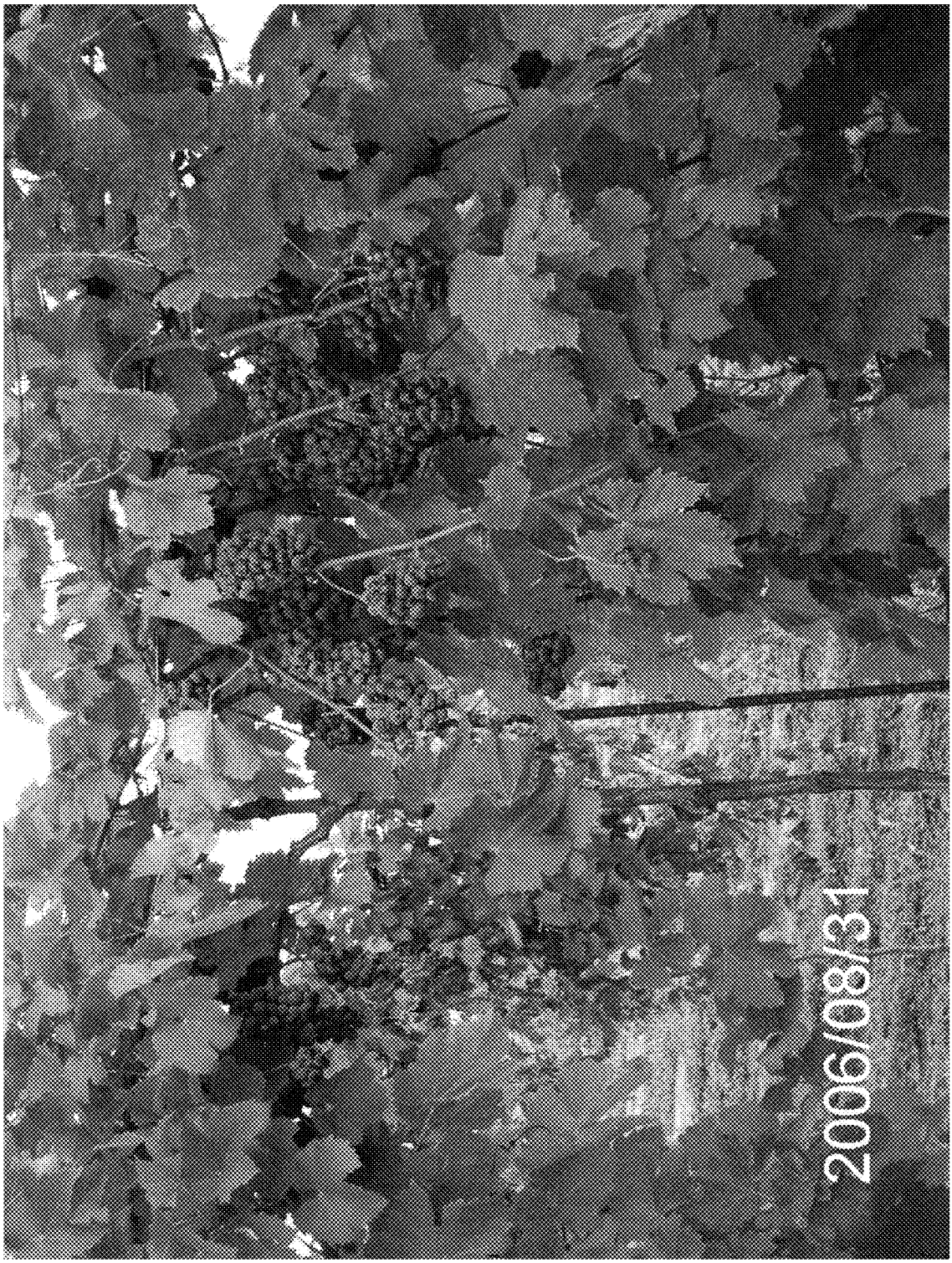
2006/08/31

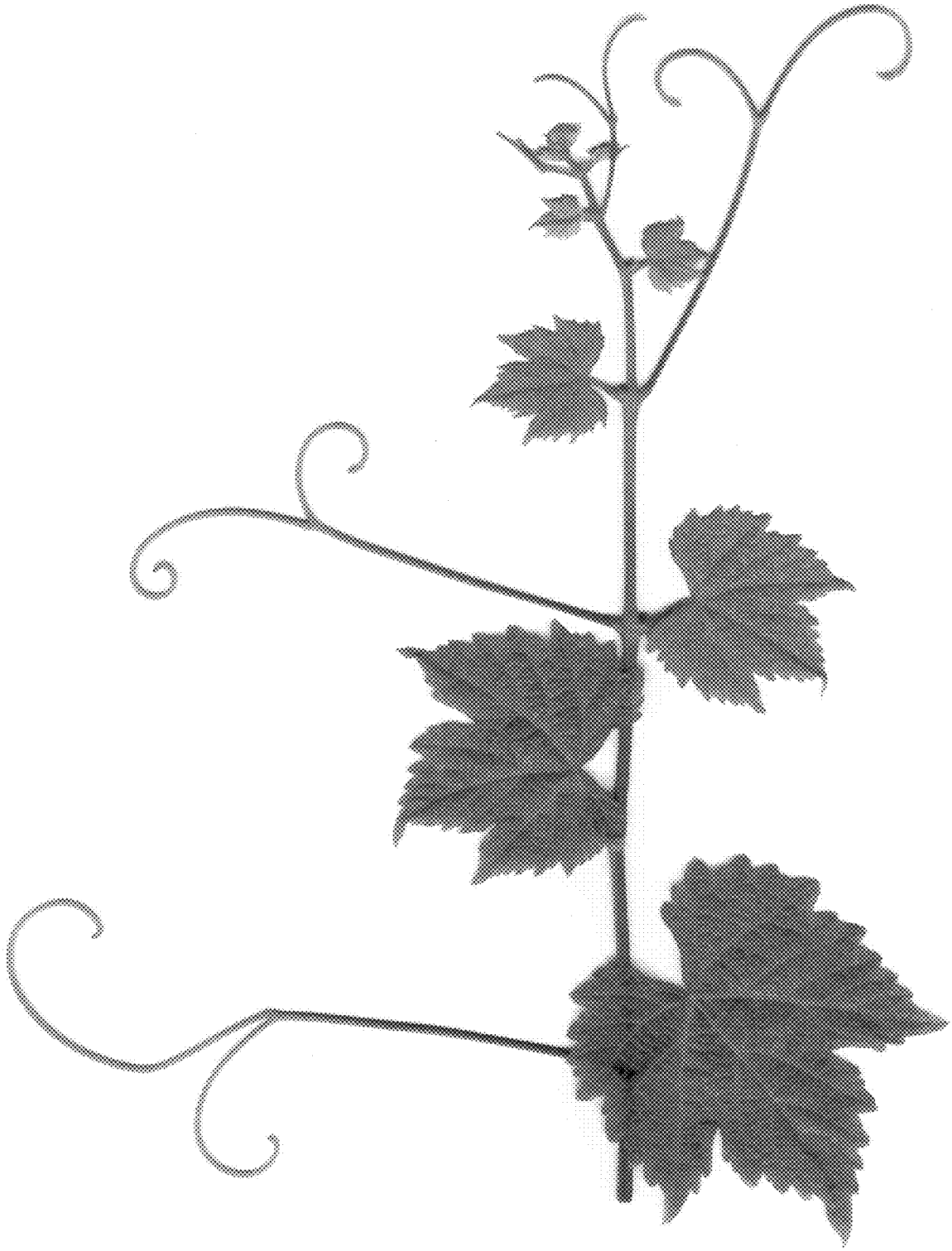

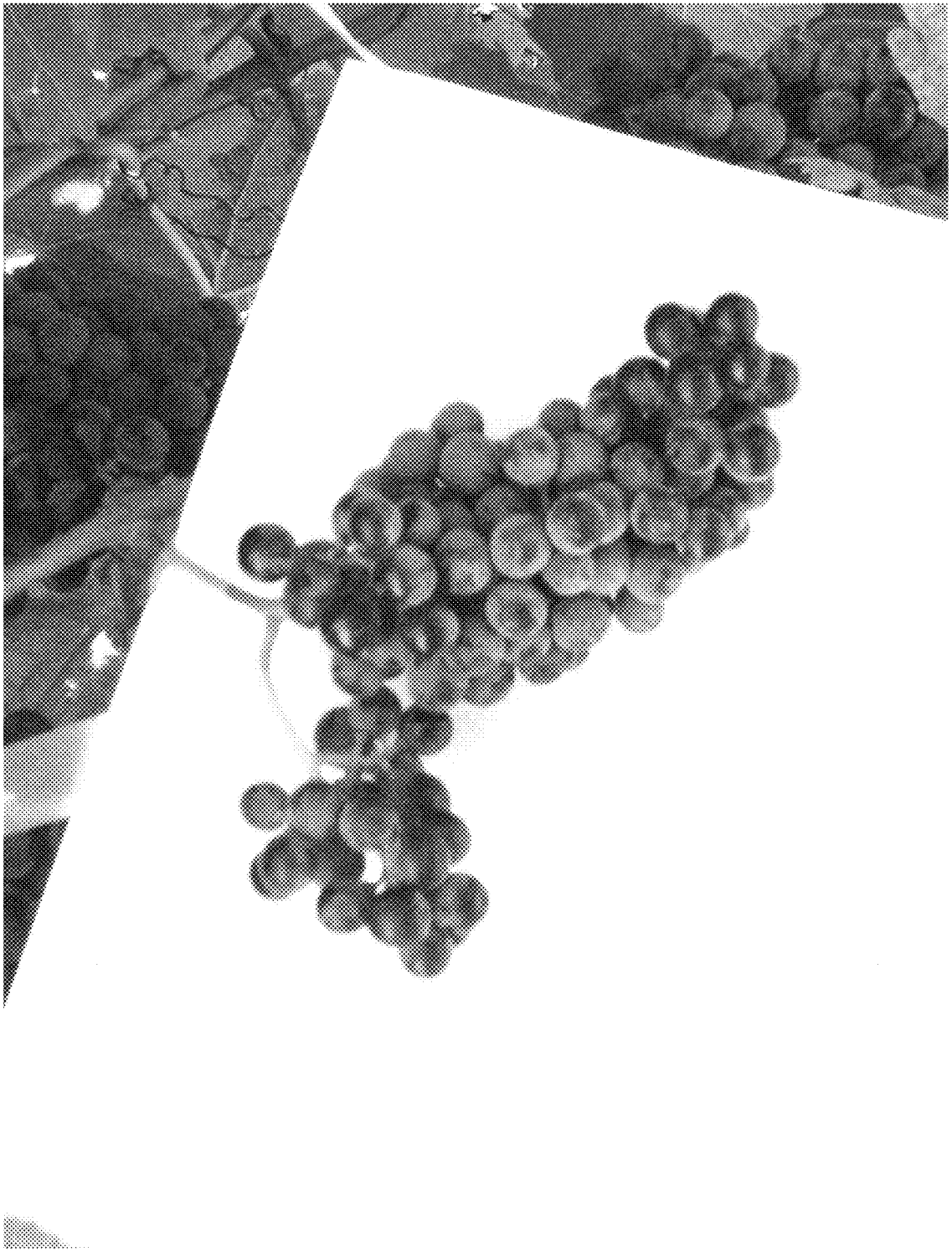

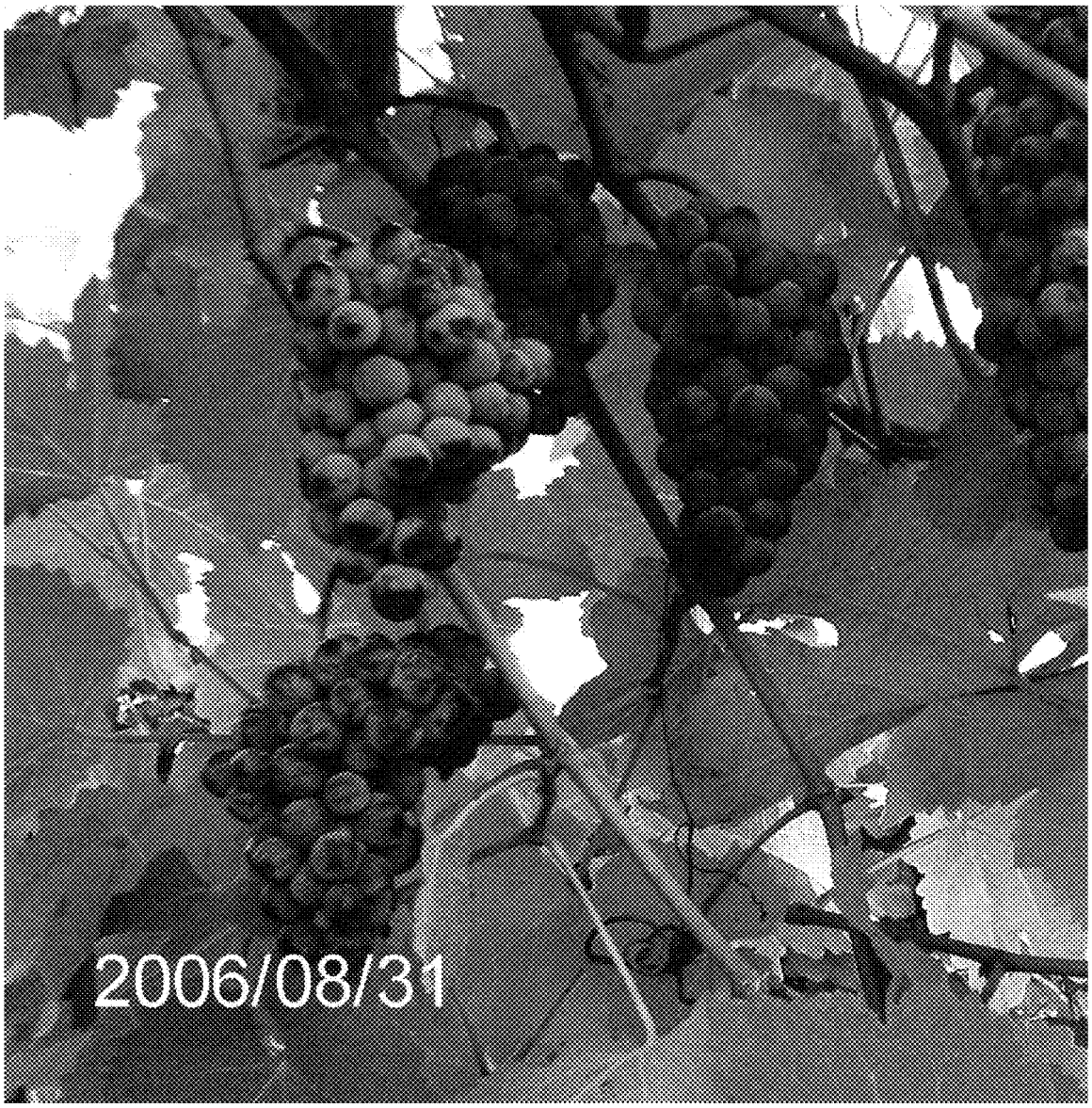
2006/08/31